US008383833B2

(12) United States Patent
Yamamoto et al.

(10) Patent No.: US 8,383,833 B2
(45) Date of Patent: Feb. 26, 2013

(54) METHOD FOR PRODUCING OPTICALLY ACTIVE AMINO ACID DERIVATIVE

(75) Inventors: Shohei Yamamoto, Takasago (JP); Akio Fujii, Takasago (JP); Masaru Mitsuda, Takasago (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 12/993,661

(22) PCT Filed: Jun. 2, 2009

(86) PCT No.: PCT/JP2009/060050
§ 371 (c)(1),
(2), (4) Date: Jan. 14, 2011

(87) PCT Pub. No.: WO2009/148046
PCT Pub. Date: Dec. 10, 2009

(65) Prior Publication Data
US 2011/0166354 A1 Jul. 7, 2011

(30) Foreign Application Priority Data
Jun. 3, 2008 (JP) ................................ 2008-145882

(51) Int. Cl.
*C07D 295/03* (2006.01)
(52) U.S. Cl. ...................................................... 548/540
(58) Field of Classification Search ........................ None
See application file for complete search history.

(56) References Cited

PUBLICATIONS

Reider, PJ. et al. An Asymmetric Synthesis of 3-aryl-1,4-oxazin-2-ones:Synthesis of a Key Intermediate of an NK1 Receptor Antagonist. Heterocycles. 2002, vol. 58, p. 120 and 122.*
Reider, PJ. et al. An Asymmetric Synthesis of 3-Aryl-1,4-oxazin-2-ones: Synthesis of a Key Intermediate of an NK1 Receptor Antagonist. Heterocycles. 2002, vol. 58, p. 120, table 1.*
March, J. et al. Mar.'s Advanced Organic Chemistry. Wiley. 2007, p. 1419-1421.*
Fuming, M. et al. A novel catalyst for transesterfication of dimethyl carbonate with phenyl to diphenyl carbonate: samarium trifluoromethanesulfonate. Journal of Molecular Catalysis A. 2002, vol. 184, p. 466, table 1.*
Kurti, L. et al. Strategic Applications of Named Reactions in Organic Synthesis. El Sevier. 2005, p. 200, top reaction scheme.*
Tricca, ML. et al. Asymmetric Synthesis of Arylpropionic Acids and Aryloxy Acids by Using Lactamides as Chiral Auxiliaries. Eur. J. Org. Chem. 2006, p. 4089, right column, lines 1-4, p. 4090, scheme 2.*
Momose, T. et al. 2(3H)-AND 2(5H)-Furanones. VII.1 Chirality Transfer on the Tetronic Acid Templates. Heterocycles. 1999, vol. 51, p. 1322.*
Verkade, JMM. et al. Mild and Efficient Deprotection of the amine protecting p-methoxyphenyl (PMP) group. Tetrahedron Letters. 2006, vol. 47, p. 8109, scheme 1, p. 8110, table 1.*
Carey, FA. Organic Chemistry. McGraw Hill. 2006, p. 880, Hydrolysis (sections 20.9-20.10).*
Reider et al. Heterocycles. 2002, vol. 58, 119-123.*
Koh et al., Reaction of (R)-pantolactone esters of alpha-bromoacids with amines: A remarkable synthesis of optically active alpha-amino esters, Tetrahedron Letters, 1993, vol. 34, No. 28, pp. 4473-4476.
Devine et al., An asymmetric synthesis of 3-aryl-1,4-oxazin-2-ones: Synthesis of a key intermediate of an $NK_1$ receptor antagonist, Heterocycles, 2002, vol. 58, pp. 119-123.
Zanotti et al., Base-catalysed Reactions of α-Bromo-*N* -benzyl-propionamide and -isobutyramide. Formation of 2-Amino-oxazolidinones, Journal of the Chemical Society, Perkin Transactions 1, 1980, vol. 10, pp. 2249-2253.
International Search Report issued Jun. 30, 2009 in corresponding International (PCT) Application No. PCT/JP2009/060050, of record.
International Preliminary Report on Patentability together with English translation of Written Opinion issued Jan. 20, 2011 in International Application No. PCT/JP2009/060050.
Supplementary European Search Report issued Nov. 20, 2012 in corresponding European Application No. 09758313.2.
Robert N. Ben et al., "Synthesis of Optically Active α-Amino Esters via Dynamic Kinetic Resolution: A Mechanistic Study", Journal of Organic Chemistry, 1999, vol. 64, pp. 7700-7706.
J. March, "Advanced Organic Chemistry: Reactions, mechanisms, and structure, fourth edition", John Wiley & Sons, 1992, pp. 397-398.
Yoon Min Lee et al., "(*S*)-Mandelate-Mediated Dynamic Kinetic Resolution of α-Bromo Esters for Asymmetric Syntheses of Aminoflavones, Dihydroquinoxalinones and Dihydrobenzoxazinones", Heterocycles, 2009, vol. 78, No. 9, pp. 2233-2244.

* cited by examiner

*Primary Examiner* — Jason M Nolan
*Assistant Examiner* — Ana Muresan
(74) *Attorney, Agent, or Firm* — Wenderoth, Lind & Ponack, L.L.P.

(57) ABSTRACT

The present application relates to a method for producing an optically active α-amino acid derivative, comprising steps of reacting an α-haloester derivative represented by the general formula (1):

(1)

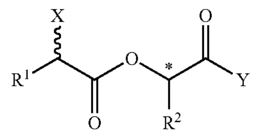

of which alcohol part of the ester group is an optically active alcohol derivative, with an amine compound; then deprotecting the obtained compound; further carrying out an ester exchange reaction. According to the present invention method, it is possible to easily produce an optically active α-amino acid ester derivative which is useful as an intermediate for drugs with high selectivity.

27 Claims, No Drawings

METHOD FOR PRODUCING OPTICALLY ACTIVE AMINO ACID DERIVATIVE

TECHNICAL FIELD

The present invention relates to a method for producing an optically active α-amino acid derivative. The optically active amino acid derivative is an intermediate which is important for producing drugs.

BACKGROUND ART

An optically active α-amino acid derivative can be produced by, for example, deprotecting and hydrolyzing an optically active N-protected α-amino acid derivative represented by the general formula (3).

(3)

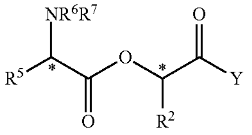

Such an optically active N-protected α-amino acid ester derivative can be synthesized by, for example, stereoselective amination of an α-haloester having a certain structure. As the method, for example, the following methods have been known:

i) The method in which an α-bromoester having a pantolactone as chiral auxiliaries is aminated (Non-Patent Reference 1); and ii) The method in which an α-bromoester having a lactic pyrrolidine amide as chiral auxiliaries is aminated (Non-Patent Reference 2).

PRIOR ART

Non-Patent References

Non-Patent Reference 1: Tetrahedron Letters, 1993, vol. 34, p. 4473

Non-Patent Reference 2: Heterocycles, 2002, vol. 58, p. 4473

DISCLOSURE OF THE INVENTION

Problems to be Solved by the Invention

The above method i) has a problem that the chiral auxiliaries are expensive. In addition, the above method ii) has problems that there is no versatile method for easily-removing the chiral auxiliary group at low cost and high selectivity cannot be achieved when $R^1$ of the α-bromoester derivative is an alkyl group.

Means for Solving the Problems

The present inventors earnestly studied the method for producing an optically active α-amino acid derivative which is an important intermediate for drugs and the like with high selectivity from various substrates using only inexpensive and easily-available raw material compounds and reagents in view of the problems of conventional methods. As a result, the present inventors developed the general method for synthesizing optically active amino acid derivatives by reacting an α-haloester derivative having an optically active alcohol derivative in the ester group with an amine compound, subsequently-deprotecting, and carrying out ester exchange or hydrolysis. In addition, it became possible by using an arylamine compound that the amino acid derivatives which do not have aryl group at α-position are high-selectively synthesized.

The present invention relates to a method for producing an optically active N-protected α-amino acid ester derivative, comprising the steps of a) reacting an α-haloester derivative represented by the general formula (1):

(1)

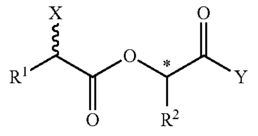

wherein, $R^1$ is an optionally substituted alkyl group having 1 to 12 carbon atoms, an optionally substituted aryl group having 6 to 14 carbon atoms, or an optionally substituted aralkyl group having 7 to 15 carbon atoms; $R^2$ is an optionally substituted alkyl group having 1 to 12 carbon atoms, an optionally substituted aryl group having 6 to 14 carbon atoms, or an optionally substituted aralkyl group having 7 to 15 carbon atoms; Y is an optionally substituted alkyloxy group having 1 to 12 carbon atoms, an optionally substituted monoalkylamino group having 1 to 12 carbon atoms, or an optionally substituted dialkylamino group having 1 to 12 carbon atoms; X is a halogen atom; * indicates an asymmetric carbon atom, with an amine compound represented by the general formula (2):

$HNR^3R^4$ (2)

wherein, $R^3$ and $R^4$ may be the same or different from each other, and are a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group; and $R^3$ may be linked with $R^4$ to form a ring, to obtain an optically active N-protected α-amino acid ester derivative represented by the general formula (3):

(3)

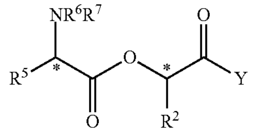

wherein, $R^5$ is the same as the above $R^1$ or may be linked with $R^6$ to form a ring; $R^6$ is the same as the above $R^3$ or may be linked with $R^5$ to form a ring; $R^7$ is the same as the above $R^4$; $R^2$ and Y are the same as the above; * indicates an asymmetric carbon;

b) conducting ester exchange of the above N-protected α-amino acid ester derivative represented by the formula (3) with an alcohol represented by the general formula (4):

$R^8OH$ (4)

wherein, $R^8$ is an optionally substituted alkyl group having 1 to 12 carbon atoms, an optionally substituted aryl group having 6 to 14 carbon atoms, or an optionally substituted aralkyl group having 7 to 15 carbon atoms;

wherein the optically active N-protected α-amino acid ester derivative is represented by the general formula (5):

(5)

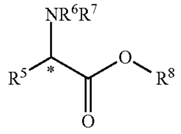

wherein, $R^5$, $R^6$, $R^7$, $R^8$ and * are the same as the above.

In addition, the present invention relates to an α-haloester derivative represented by the formula (9):

(9)

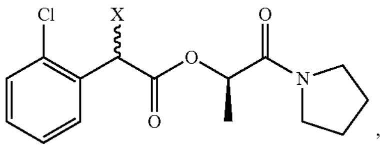

, and an optically active N-protected α-amino acid ester derivative represented by the formula (10):

(10)

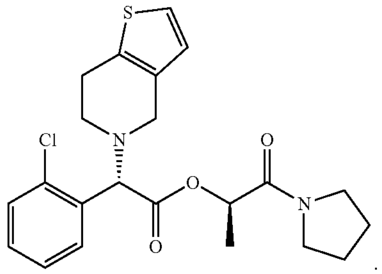

.

Further, the present invention relates to a method for producing an optically active α-amino acid derivative, comprising the steps of a) reacting an α-haloester derivative represented by the formula (1) with an amine compound represented by the formula (2), to obtain an optically active N-protected α-amino acid ester derivative represented by the formula (3);

c) cleaving the substituent group on the N atom of the N-protected α-amino acid ester derivative represented by the formula (3), to obtain an α-amino acid ester derivative represented by the general formula (11):

(11)

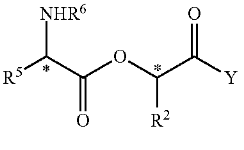

wherein, $R^2$, $R^5$, $R^6$, Y and * are the same as the above;

d) hydrolyzing the α-amino acid ester derivative represented by the formula (11);

wherein the optically active α-amino acid derivative is represented by the general formula (12):

(12)

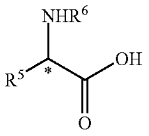

wherein, $R^5$, $R^6$ and * are the same as the above.

Furthermore, the present invention relates to a method for producing an optically active N-protected α-amino acid derivative, comprising the steps of a) reacting an α-haloester derivative represented by the formula (1) with an amine compound represented by the formula (2), to obtain an optically active α-N-protected amino acid ester derivative represented by the formula (3);

e) hydrolyzing the N-protected α-amino acid ester derivative represented by the formula (3);

wherein the optically active N-protected α-amino acid derivative is represented by the general formula (13):

(13)

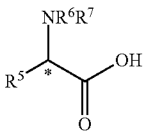

wherein, $R^5$, $R^6$, $R^7$ and * are the same as the above.

Effect of the Invention

According to the production method of the present invention, it is possible to easily-produce an optically active amino acid derivative which is useful as an intermediate for drugs from inexpensive and easily-obtainable raw material. In particular, optical purity is remarkably decreased during the step for removing an optically active alcohol from an optically active N-protected α-amino acid ester derivative having the optically active alcohol in the ester part according to conventional methods; on the other hand, it becomes possible by the present invention to prevent the pronounced decrease of optical purity and effectively-carry out the reaction. As a result, it becomes possible to effectively-synthesize an N-protected α-amino acid ester derivative and an N-protected α-amino acid derivative from N-protected α-amino acid ester derivative having an optically active alcohol in the ester part.

In addition, it becomes possible by using an aryl amine in an amination reaction to high selectively-synthesize an optically active amino acid derivative which does not have an aryl group at the α-position and cannot be produced with high selectivity according to conventional methods.

MODE FOR CARRYING OUT THE INVENTION

Hereinafter, the present invention is explained in detail.

First, the first invention is explained.

1. The method for producing an optically active N-protected α-amino acid ester

In the method, an optically active N-protected amino α-acid ester derivative is produced by a) reacting an α-haloester derivative represented by the general formula (1):

(1)

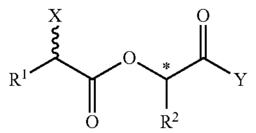

with an amine compound represented by the general formula (2):

$HNR^3R^4$ (2), to obtain an optically active N-protected α-amino acid ester derivative represented by the general formula (3):

(3)

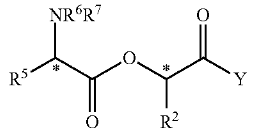

b) conducting ester exchange of the above N-protected α-amino acid ester derivative represented by the formula (3) with an alcohol represented by the general formula (4):

$R^8OH$ (4)

wherein the optically active N-protected α-amino acid ester derivative is represented by the general formula (5):

(5)

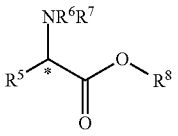

In the formula (1), $R^1$ is an optionally substituted alkyl group having 1 to 12 carbon atoms, an optionally substituted aryl group having 6 to 14 carbon atoms, or an optionally substituted aralkyl group having 7 to 15 carbon atoms; and is specifically exemplified by, for example, a phenyl group, a 4-chlorophenyl group, a 3-chlorophenyl group, a 2-chlorophenyl group, a 4-fluorophenyl group, a 3-fluorophenyl group, a 2-fluorophenyl group, a 4-bromophenyl group, a 3-bromophenyl group, a 2-bromophenyl group, a 4-trifluoromethylphenyl group, a 3-trifluoromethylphenyl group, a 2-trifluoromethylphenyl group, a 1-naphthyl group, a 2-naphthyl group, a 4-methylphenyl group, a 3-methylphenyl group, a 2-methylphenyl group, a 4-ethylphenyl group, a 3-ethylphenyl group, a 2-ethylphenyl group, a 4-methoxyphenyl group, a 3-methoxyphenyl group, a 2-methoxyphenyl group, a 4-nitrophenyl group, a 4-phenylphenyl group, a methyl group, an ethyl group, an n-propyl group, an i-propyl group, an n-butyl group, an i-butyl group, a t-butyl group, a benzyl group, a methylcyclopropyl group, a 4-bromobutyl group, a 3-bromobutyl group, a 2-bromobutyl group, a 5-bromopentyl group, a 4-bromopentyl group, a 3-bromopentyl group, a 2-bromopentyl group, a phenylmethyl group, a 2-phenylethyl group, a 1-phenylethyl group, a 3-phenylbutyl group, a 2-phenylbutyl group, a 1-phenylbutyl group.

$R^2$ is an optionally substituted alkyl group having 1 to 12 carbon atoms, an optionally substituted aryl group having 6 to 14 carbon atoms, or an optionally substituted aralkyl group having 7 to 15 carbon atoms; and is exemplified by, for example, a methyl group, an ethyl group, an n-propyl group, an n-butyl group, a phenyl group, a 4-methylphenyl group, a naphthyl group, a benzyl group; and is preferably a methyl group, an ethyl group, a phenyl group, a benzyl group; and is more preferably a methyl group.

X is a halogen atom, and is specifically a chlorine atom, a bromine atom or an iodine atom.

Y is an optionally substituted alkyloxy group having 1 to 12 carbon atoms, an optionally substituted monoalkylamino group having 1 to 12 carbon atoms, or an optionally substituted dialkylamino group having 1 to 12 carbon atoms; and is exemplified by, for example, a methoxy group, an ethoxy group, a t-butoxy group, a pyrrolidinyl group, a piperidinyl group, a morphonyl group, a dimethylamino group, a diethylamino group, a dibenzylamino group, a benzylamino group, a t-butylamino group; and is preferably a pyrrolidinyl group, a piperidinyl group, a morphonyl group, and is more preferably a pyrrolidinyl group.

The "*" indicates an asymmetric carbon atom.

The α-haloester derivative represented by the formula (1) can be produced by, for example, f) reacting a carboxylic acid represented by the general formula (6):

(6)

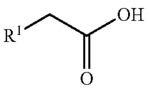

with phosphorus tribromide and bromine, to obtain a compound represented by the general formula (7):

(7)

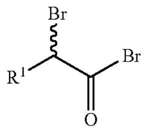

and g) reacting the compound (7) with an alcohol represented by the general formula (8):

(8)

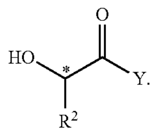

In the formulae (6) and (7), $R^1$ is the same as the above.

In the formula (8), $R^2$, Y and * are the same as the above.

In the formula (2), $R^3$ and $R^4$ may be the same or different from each other; and are a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group.

$R^3$ and $R^4$ are specifically exemplified by, for example, a hydrogen atom, a phenyl group, a 4-chlorophenyl group, a 3-chlorophenyl group, a 2-chlorophenyl group, a 4-fluorophenyl group, a 3-fluorophenyl group, a 2-fluorophenyl group, a 4-bromophenyl group, a 3-bromophenyl group, a 2-bromophenyl group, a 4-trifluoromethylphenyl group, a 3-trifluoromethylphenyl group, a 2-trifluoromethylphenyl group, a 1-naphthyl group, a 2-naphthyl group, a 4-methylphenyl group, a 3-methylphenyl group, a 2-methylphenyl group, a 4-ethylphenyl group, a 3-ethylphenyl group, a 2-ethylphenyl group, a 4-methoxyphenyl group, a 3-methoxyphenyl group, a 2-methoxyphenyl group, a 4-nitrophenyl group, a 4-phenylphenyl group, a methyl group, an ethyl group, an n-propyl group, an i-propyl group, an n-butyl group, an i-butyl group, a t-butyl group, a benzyl group, a methylcyclopropyl group, a 4-bromobutyl group, a 3-bromobutyl group, a 2-bromobutyl group, a 5-bromopentyl group, a 4-bromopentyl group, a 3-bromopentyl group, a 2-bromopentyl group, a phenylmethyl group, a 2-phenylethyl group, a 1-phenylethyl group, a 3-phenylbutyl group, a 2-phenylbutyl group, a 1-phenylbutyl group, an o-nitrobenzenesulfonyl group, an m-nitrobenzenesulfonyl group, a p-nitrobenzenesulfonyl group, an o-toluenesulfonyl group, an m-toluenesulfonyl group, a p-toluenesulfonyl group, a methylcarbonyl group, an ethylcarbonyl group, an n-propylcarbonyl group, an i-propylcarbonyl group, an n-butylcarbonyl group, an i-butylcarbonyl group, a t-butylcarbonyl group, a benzylcarbonyl group, a methylcyclopropylcarbonyl group, a methoxycarbonyl group, an ethoxycarbonyl group, an n-propoxycarbonyl group, an i-propoxycarbonyl group, an n-butoxycarbonyl group, an i-butoxycarbonyl group, a t-butoxycarbonyl group, a benzyloxycarbonyl group, a methylcyclopropoxycarbonyl group.

$R^3$ may be linked with $R^4$ to form a ring. Such a ring is exemplified by, for example, an aziridine ring, a pyrrolidine ring and a piperidine ring. The amine represented by the general formula (2) having a ring is exemplified by, for example, 4,5,6,7-tetrahydrothieno[3,2-c]pyridine.

It is preferable in terms of the selectivity of the amination reaction that at least one of $R^3$ and $R^4$ is an aryl group. In particular, such an aryl group is more preferably a p-methoxyphenyl group or an o-methoxyphenyl group, since the groups can be easily-cleaved from the N atom when at least one of $Br_2$, trichloroisocyanuric acid, N-bromosuccinimide, N-chlorosuccinimide and $H_5IO_6$ is reacted with an optically active N-protected α-amino acid ester derivative under acidic condition.

In the formula (3), $R^2$, Y and * are the same as the above.

Since $R^5$ corresponds to $R^1$, $R^5$ is exemplified by the same groups as those described as $R^1$. In addition, $R^5$ may be linked with $R^6$ to form a ring.

Since $R^6$ corresponds to $R^3$, $R^6$ is exemplified by the same groups as those described as $R^3$. In addition, $R^6$ may be linked with $R^5$ to form a ring.

Since $R^7$ corresponds to $R^4$, $R^7$ is exemplified by the same groups as those described as $R^4$.

In the formula (4), $R^8$ is an optionally substituted alkyl group having 1 to 12 carbon atoms, an optionally substituted aryl group having 6 to 14 carbon atoms, or an optionally substituted aralkyl group having 7 to 15 carbon atoms.

$R^8$ is specifically exemplified by, for example, a methyl group, an ethyl group, an n-propyl group, an i-propyl group, an n-butyl group, an i-butyl group, a t-butyl group, a benzyl group, a methylcyclopropyl group, a phenyl group, a 4-chlorophenyl group, a 3-chlorophenyl group, a 2-chlorophenyl group, a 4-fluorophenyl group, a 3-fluorophenyl group, a 2-fluorophenyl group, a 4-bromophenyl group, a 3-bromophenyl group, a 2-bromophenyl group, a 4-trifluoromethylphenyl group, a 3-trifluoromethylphenyl group, a 2-trifluoromethylphenyl group, a 1-naphthyl group, a 2-naphthyl group, a 4-methylphenyl group, a 3-methylphenyl group, a 2-methylphenyl group, a 4-ethylphenyl group, a 3-ethylphenyl group, a 2-ethylphenyl group, a 4-methoxyphenyl group, a 3-methoxyphenyl group, a 2-methoxyphenyl group, a 4-nitrophenyl group, a 4-phenylphenyl group.

$R^8$ is preferably a methyl group, an ethyl group, an n-propyl group, an i-propyl group, an n-butyl group, an i-butyl group, a t-butyl group, a benzyl group; and is particularly preferably a methyl group.

In the formula (5), $R^5$, $R^6$, $R^7$, $R^8$ and * are the same as the above.

Next, the reaction condition is explained.

The solvent used in the step (a) is not particularly limited; and hydrocarbon solvents such as toluene, n-hexane and cyclohexane; ether solvents such as diethyl ether, tetrahydrofuran, 1,4-dioxane, methyl t-butyl ether, dimethoxyethane and ethylene glycol dimethyl ether; halogenated solvents such as methylene chloride, 1,2-dichloroethane and chlorobenzene; nitrogen-containing solvents such as acetonitrile, acetoamide, dimethylformamide and dimethylacetoamide; alcohol solvents such as methanol, ethanol, isopropanol and t-butanol can be used. One of the solvent may be used by itself, or plural solvents may be used in combination. The solvent is preferably toluene and tetrahydrofuran.

The use amount of the amine represented by the formula (2) is 0.8 times by mole to 3 times by mole, and preferably 1.0 time by mole to 1.3 times by mole, relative to the α-bromoester derivative.

The amine represented by the formula (2) may be directly used, or may be dissolved in a solvent to be used. The solvent is not particularly limited, but, for example, hydrocarbon solvents such as toluene, benzene, n-hexane and cyclohexane; ether solvents such as diethyl ether, tetrahydrofuran, 1,4-dioxane, methyl t-butyl ether, dimethoxyethane and ethylene glycol dimethyl ether; ketone solvents such as acetone, methyl ethyl ketone and t-butyl methyl ketone; alkylester solvents such as ethyl acetate, propyl acetate and butyl acetate; halogenated solvents such as methylene chloride, 1,2-dichloroethane and chlorobenzene; nitrogen-containing solvents such as acetonitrile, acetoamide, dimethylformamide and dimethylacetoamide; alcohol solvents such as methanol, ethanol, isopropanol and t-butanol can be used as the solvent. One of the solvent may be used by itself, or plural solvents may be used in combination. The solvent is preferably toluene and tetrahydrofuran.

The reaction temperature is preferably −20° C. to 160° C., more preferably −10° C. to 60° C., and particularly preferably −10° C. to 40° C.

The reaction may proceeds without using a base; however, a base is preferably used. The base to be used is not particularly limited; but, is preferably, for example, amine bases such as triethylamine, N,N-diisopropylethylamine and pyridine, and inorganic bases such as potassium carbonate, sodium carbonate and lithium carbonate, and is particularly preferably triethylamine and pyridine.

In the reaction, an additive reagent may not be particularly used; however, it is preferably that the reaction carried out in the presence of an iodide ion by using an additive reagent for high selectivity. The additive reagent is exemplified by inorganic salts such as lithium iodide, sodium iodide, potassium iodide, magnesium iodide and calcium iodide; quaternary ammonium salts such as tetrabutylammonium iodide, tetrapentylammonium iodide and tetrahexylammonium iodide. The additive reagent is preferably sodium iodide, potassium iodide, tetrabutylammonium iodide, and is particularly preferably sodium iodide.

The use amount of the additive reagent is 0.01 times by mole to 3 times by mole, and preferably 0.1 times by mole to 1.5 times by mole, relative to the α-bromoester derivative.

After the reaction, a general procedure may be carried out for purifying the target compound. For example, the pH of the reaction mixture is adjusted after the reaction if needed, and then extraction procedure is carried out using a general solvent such as ethyl acetate, diethylether, methylene chloride, toluene and hexane. The reaction solvent and extraction solvent are distilled away from the obtained extract by heating under reduced pressure to obtain the target compound. In addition, the same procedure may be carried out after the reaction solvent is distilled away by heating under reduced pressure immediately after the reaction is completed, or the reaction solvent may be distilled away after water is added if needed.

In the reaction, high selectivity can be achieved compared to the method described in Non-Patent Reference 2 by using an arylamine as a nitrogen nucleophile, in particular, when $R^1$ and $R^5$ in the formulae (1) and (3) are alkyl groups.

In the step (b), an optically active N-protected α-amino acid ester derivative represented by the general formula (5) is obtained by ester exchange of the optically active N-protected α-amino acid ester derivative which is represented by the formula (3) and obtained by the step (a) with an alcohol represented by the general formula (4).

The reaction may be carried out under acidic condition or basic condition. The reaction is preferably carried out under acidic condition, and more preferably in the presence of sulfuric acid, hydrochloric acid, methanesulfonic acid, trifluoromethanesulfonic acid, p-toluenesulfonic acid or Lewis acid, and particularly preferably in the presence of aluminium chloride or titanium tetraisopropoxide.

The use amount of the acid to be used is 0.1 times by equivalent amount to 100 times by equivalent amount, preferably 0.1 times by equivalent amount to 20 times by equivalent amount, and particularly preferably 0.1 times by equivalent amount to 10 times by equivalent amount.

The use amount of the alcohol which is used in the step and represented by the formula (4) is 1 time by equivalent amount to 200 times by equivalent amount, preferably 2 times by equivalent amount to 100 times by equivalent amount, and more preferably 5 times by equivalent amount to 50 times by equivalent amount, relative the N-protected α-amino acid ester derivative.

The reaction temperature is preferably 10° C. to 160° C., more preferably 20° C. to 100° C., and particularly preferably 40° C. to 70° C.

In the step, a side reaction and racemization can be prevented and the reaction can be promptly completed, in particular, at least one of aluminium chloride and titanium tetraisopropoxide is used.

In the step (f), a solvent is not particularly needed; but an aprotic solvent may be used. For example, hydrocarbon solvents such as toluene, n-hexane and cyclohexane; ether solvents such as diethyl ether, tetrahydrofuran, 1,4-dioxane, methyl t-butyl ether, dimethoxyethane and ethylene glycol dimethyl ether; halogenated solvents such as methylene chloride, 1,2-dichloroethane and chlorobenzene; nitrogen-containing solvents such as acetonitrile, acetoamide, dimethylformamide and dimethylacetoamide may be used. One of the solvents may be used by itself, or plural solvents may be used in combination. Preferably, a solvent is not used.

The use amount of $PBr_3$ is 0.1 times by mole to 2 times by mole, and preferably 0.3 times by mole to 1.0 time by mole, relative to the carboxylic acid.

The use amount of $Br_2$ is 1.0 time by mole to 4 times by mole, and preferably 1.2 times by mole to 1.8 time by mole, relative to the carboxylic acid.

The reaction temperature is preferably 0° C. to 120° C., and more preferably 40° C. to 100° C.

In the step (g), a solvent is not particularly needed; but an aprotic solvent may be used. For example, hydrocarbon solvents such as toluene, n-hexane and cyclohexane; ether solvents such as diethyl ether, tetrahydrofuran, 1,4-dioxane, methyl t-butyl ether, dimethoxyethane and ethylene glycol dimethyl ether; halogenated solvents such as methylene chloride, 1,2-dichloroethane and chlorobenzene; nitrogen-containing solvents such as acetonitrile, acetoamide, dimethylformamide and dimethylacetoamide may be used. One of the solvents may be used by itself, or plural solvents may be used in combination. The solvent is preferably toluene and tetrahydrofuran.

The use amount of the alcohol represented by the formula (8) is 0.8 times by mole to 3 times by mole, and preferably 1.0 time by mole to 1.3 times by mole, relative to the acid bromide represented by the formula (7).

The reaction temperature is preferably 0° C. to 100° C., and more preferably 20° C. to 60° C.

Next, the second invention is explained.

2. The method of producing a optically active α-amino acid derivative

In the method, an optically active α-amino acid derivative represented by the general formula (12):

(12)

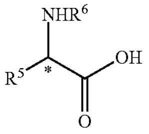

is produced by a) reacting an α-haloester derivative represented by the formula (1) with an amine compound represented by the formula (2), to obtain an optically active N-protected α-amino acid ester derivative represented by the formula (3);

c) cleaving the substituent group on the N atom of the N-protected α-amino acid ester derivative represented by the formula (3), to obtain an α-amino acid ester derivative represented by the general formula (11):

(11)

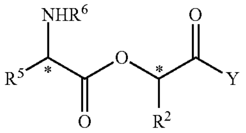

d) hydrolyzing the α-amino acid ester derivative represented by the formula (11).

By the method, it becomes possible to easily-produce an optically active α-amino acid derivative at low cost. In particular, it also becomes to possible to synthesize amino acid which does not have an aryl group at α-position by using an aryl amine with high selectivity.

The formulae (1) to (3) are explained as the above.

In the formula (11), $R^2$, $R^5$, $R^6$, Y and * are the same as the above.

In the formula (12), $R^5$, $R^6$ and * are the same as the above.

Next, the reaction condition is explained.

In the reaction, the condition of the step (a) is explained as the above.

In the step (c), an optically active α-amino acid ester derivative represented by the formula (11) can be obtained by cleaving (removing) the substituent group on the N atom of the N-protected α-amino acid ester derivative which is obtained by the step (a) and represented by the formula (3).

As the general method for cleaving the substituent group on the N atom, for example, hydrogenation reaction using a carbon-supported palladium catalyst is exemplified when $R^7$ is a benzyl derivative; deprotection reaction using an alkylthiol is exemplified when $R^7$ is a 2-nitrobenzenesulfonyl group; and oxidative deprotection reaction using cerium ammoniumnitrate is exemplified when $R^7$ is a methoxyphenyl group. In particular, the substituent on the N atom can be effectively cleaved by using at least one of $Br_2$, trichloroisocyanuric acid, N-bromosuccinimide, N-chlorosuccinimide and $H_5IO_6$ when $R^7$ is a methoxyphenyl group.

In the step (d), an optically active α-amino acid represented by the formula (12) is obtained by hydrolyzing the optically active α-amino acid ester derivative which is obtained by the step (c) and represented by the formula (11).

The condition of the hydrolysis may be acidic condition or basic condition. Specifically, the hydrolysis can be carried out using alkali metal hydroxides such as lithium hydroxide, sodium hydroxide and potassium hydroxide; alkaline earth metal hydroxides such as magnesium hydroxide, calcium hydroxide and barium hydroxide; mineral acid; hydrochloric acid, sulfuric acid, hydrobromic acid, methanesulfonic acid, trifluoromethanesulfonic acid, p-toluenesulfonic acid, acetic acid, trifluoroacetic acid or formic acid.

The reaction temperature of the step is preferably 0° C. to 100° C., and more preferably 10° C. to 50° C. The use amount of the acid or base is 1 time by equivalent amount to 20 times by equivalent amount, preferably 1 time by equivalent amount to 5 times by equivalent amount.

Next, the third invention is explained.

3. The method for producing an optically active N-protected α-amino acid

In the method, an optically active N-protected α-amino acid derivative represented by the general formula (13):

(13)

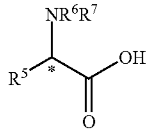

is produced by a) reacting an α-haloester derivative represented by the formula (1) with an amine compound represented by the formula (2), to obtain an optically active N-protected α-amino acid ester derivative represented by the formula (3);

e) hydrolyzing the N-protected α-amino acid ester derivative represented by the formula (3).

The formulae (1) to (3) are the same as the above.

In the formula (13), $R^5$, $R^6$, $R^7$ and * are the same as the above.

Next, the reaction condition is explained.

In the reaction, the condition of the step (a) is the same as the above.

In the step (e), an optically active N-protected α-amino acid represented by the formula (13) is obtained by hydrolyzing the N-protected α-amino acid ester derivative which is obtained by the step (a) and represented by the formula (3).

The condition for the hydrolysis may be acidic condition or basic condition. Specifically, alkali metal hydroxides such as lithium hydroxide, sodium hydroxide and potassium hydroxide; alkaline earth metal hydroxides such as magnesium hydroxide, calcium hydroxide and barium hydroxide; mineral acid, hydrochloric acid, sulfuric acid, hydrobromic acid, methanesulfonic acid, trifluoromethanesulfonic acid, p-toluenesulfonic acid, acetic acid, trifluoroacetic acid or formic acid may be used. Acidic condition is preferable.

The reaction temperature of the step is preferably 0° C. to 100° C., and more preferably 10° C. to 50° C. The use amount of the acid or base is 1 time by equivalent amount to 20 times by equivalent amount, preferably 1 time by equivalent amount to 5 times by equivalent amount.

EXAMPLES

The present invention is explained in more detail by examples; however, the present invention is not limited by the examples.

Example 1

Production of 2-Amino-Hexanoic Acid

(i) (1S)-1-Methyl-2-oxo-2-tetrahydro-1-H-1-pyrrolylethyl N-(p-methoxyphenyl)-2-aminohexanoate

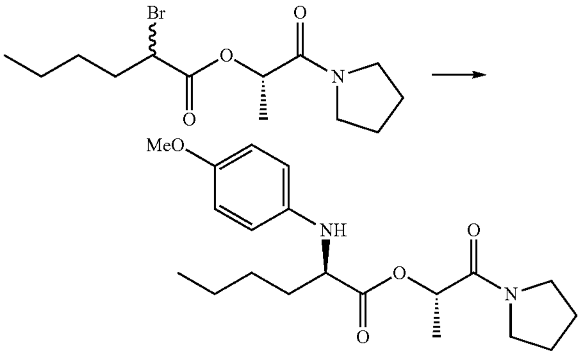

To (1R)-1-methyl-2-oxo-2-tetrahydro-1-H-1-pyrrolylethyl 2-bromohexanoate (4.8 g, 15 mmol), NaI (2.3 g, 15 mmol), triethylamine (2.4 g, 24 mmol) and tetrahydrofuran (5 mL) were added. To the solution, p-methoxyaniline (2.4 g, 20 mmol) and tetrahydrofuran (5 mL) were added. The mixture was stirred at 37° C. for 1 hour and then at 20° C. for 5 hours. To the mixture, a saturated sodium sulfite aqueous solution and ethyl acetate were added for extraction. The obtained extract was dried with anhydrous magnesium sulfate, and then the solvent was removed away in reduced pressure in order to obtain 8.2 g of oil. The conversion ratio to the obtained compound was 1000, and the diastereo ratio calculated by NMR analysis was 94.5:5.5.

(ii) 2-Amino-hexanoic Acid

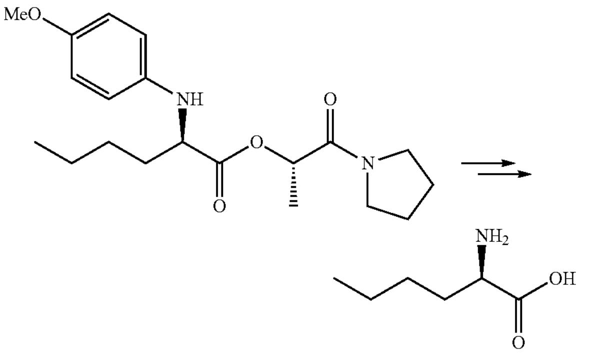

To the compound obtained in the step (i), acetonitrile (15 mL) and water (10 mL) were added, and then trichloroisocyanuric acid (1.7 g, 7.5 mmol) and 1M sulfuric acid (15 mL) were added. The mixture was stirred at room temperature for 3 hours. To the mixture, trichloroisocyanuric acid (1.7 g, 7.5 mmol) was further added. The mixture was stirred at room temperature for 2 hours. After it was confirmed by HPLC analysis that the compound obtained in the step (i) was completely used, dichloromethane was added and the water layer was separated. To the water layer, a 5N sodium hydroxide aqueous solution (20 mL) was added. The mixture was stirred at room temperature for 18 hours. After the water layer was washed with dichloromethane, the existence of 2-amino-hexanoic acid (1.4 g, 11 mmol, yield: 71%, 83% ee) was confirmed with HPLC analysis (Column: SUMICHIRAL OA-5000, Wavelength: 254 nm, Flow rate: 1 mL/min, Mobile phase: 2 mM $CuSO_4$ aqueous solution/IPA=95/5).

Example 2

Production of Hexahydro-2-Pyridinecarboxylic Acid (i) (1S)-1-Methyl-2-oxo-2-tetrahydro-1-H-1-pyrrolylethyl N-(p-methoxyphenyl)hexahydro-2-pyridinecarboxylate

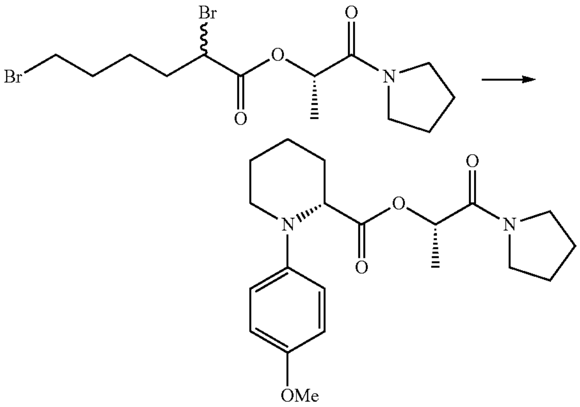

To (1R)-1-methyl-2-oxo-2-tetrahydro-1-H-1-pyrrolylethyl 2,6-dibromohexanoate (1.2 g, 3.0 mmol), NaI (0.9 g, 6.0 mmol), triethylamine (0.9 g, 9.0 mmol) and tetrahydrofuran (6 mL) were added. To the solution, p-methoxyaniline (443 mg, 3.6 mmol) and tetrahydrofuran (6 mL) were added. The mixture was stirred at 40° C. for 20 hours. To the mixture, water and ethyl acetate were added for extraction. The obtained extract was dried with anhydrous magnesium sulfate, and the solvent was removed away under reduced pressure in order to obtain 1.3 g of oil. The oil was purified with silica gel column using ethyl acetate to obtain 793 mg of white solid (2.2 mmol, yield: 73%, The diastereo ratio calculated by NMR analysis was 92:8.).

(ii) (1S)-1-Methyl-2-oxo-2-tetrahydro-1-H-1-pyrrolylethyl hexahydro-2-pyridinecarboxylate

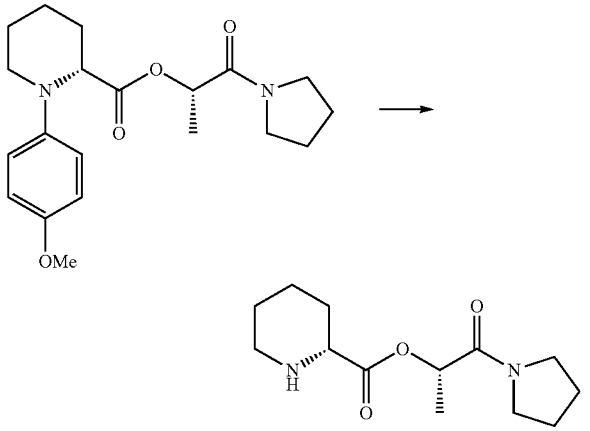

To the compound obtained in the step (i), acetonitrile (7 mL) and water (7 mL) were added, and trichloroisocyanuric acid (256 mg, 1.1 mmol) and 1M sulfuric acid (2.2 mL) were subsequently added. After the mixture was stirred at room temperature for 2 hours, trichloroisocyanuric acid (256 mg, 1.1 mmol) was added thereto. The mixture was stirred at room temperature for 2 hours. After it was confirmed by NMR analysis that the compound obtained in the step (i) was completely used, dichloromethane was added and the water layer was separated. The pH of the obtained water layer was adjusted to 10.0 using a 1N sodium hydroxide aqueous solution, and then extraction was carried out. The solvent was removed away under reduced pressure to obtain 380 mg of oil (327 mg, yield: 58%).

(iii) Hexahydro-2-pyridinecarboxylic Acid

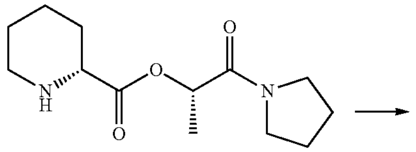

-continued

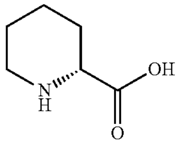

To the compound obtained in the step (ii), tetrahydrofuran (5 mL) and a 1N sodium hydroxide aqueous solution (5 mL) were added. The mixture was stirred at room temperature for 1.5 hours. After it was confirmed that the compound obtained in the step (ii) was completely used, dichloromethane was added and the water layer was separated. The existence of hexahydro-2-pyridinecarboxylic acid (146 mg, 1.1 mmol, yield: 88%, 84% ee) was confirmed with HPLC analysis (Column: SUMICHIRAL OA-5000, Wavelength: 254 nm, Flow rate: 1 mL/min, Mobile phase: 2 mM $CuSO_4$ aqueous solution/IPA=95/5).

Example 3

Production of 2-amino-3-cyclopropylbutanoic Acid

(i) (1S)-1-Methyl-2-oxo-2-tetrahydro-1-H-1-pyrrolylethyl N-(p-methoxyphenyl)-2-amino-3-cyclopropylpropanoate

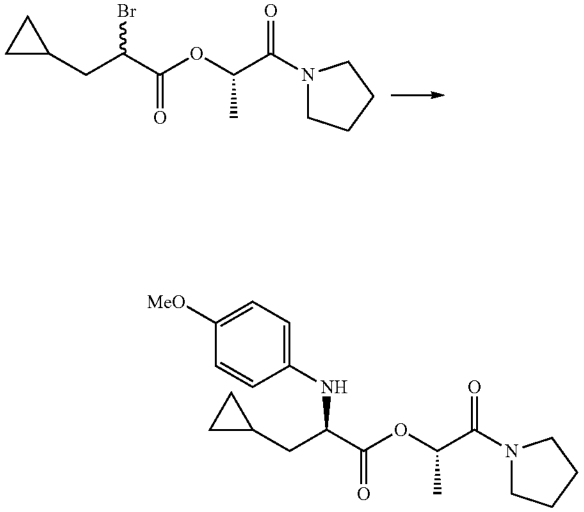

To (1S)-1-methyl-2-oxo-2-tetrahydro-1-H-1-pyrrolylethyl 2-bromo-3-cyclopropylpropanoate (418 mg, 1.3 mmol), NaI (198 mg, 1.3 mmol), triethylamine (214 g, 2.1 mmol) and tetrahydrofuran (5 mL) were added. To the solution, p-methoxyaniline (211 mg, 1.7 mmol) and tetrahydrofuran (3 mL) were added. The mixture was stirred at room temperature for 24 hours and further at 40° C. for 20 hours. To the mixture, a saturated sodium sulfite aqueous solution and ethyl acetate were added for extraction. The obtained extract was dried with anhydrous magnesium sulfate, and the solvent was removed away under reduced pressure. The residue was purified with silica gel chromatography to obtain 270 mg of the target compound (yield: 57%, The diastereo ratio calculated by NMR analysis was 92:8.).

(ii) 2-Amino-3-cyclopropylbutanoic Acid

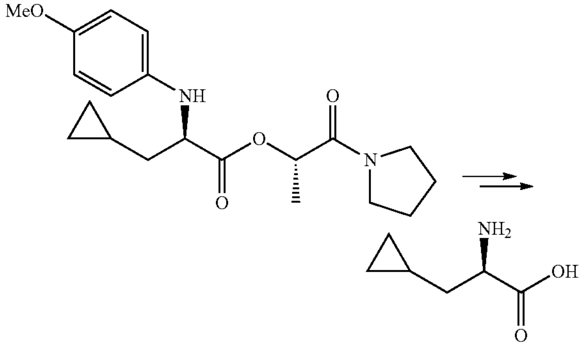

To the compound obtained in the step (i) (270 mg, 0.75 mmol), acetonitrile (3 mL) and water (2 mL) were added, and trichloroisocyanuric acid (87 mg, 0.38 mmol) and 1M sulfuric acid (0.75 mmol) were further added. The mixture was stirred at room temperature for 1 hour. After it was confirmed that the raw material compound was completely used, a 1N sodium hydroxide aqueous solution (3 mL) was added. The mixture was stirred at room temperature for 3 hours. Subsequently, a 5N sodium hydroxide aqueous solution (1 mL) was added thereto, and the mixture was stirred at room temperature for 12 hours. The optical purity of the obtained target compound was 82% ee by HPLC analysis (Column: SUMICHIRAL OA-5000, Wavelength: 254 nm, Flow rate: 1 mL/min, Mobile phase: 2 mM $CuSO_4$ aqueous solution/IPA=95/5).

Example 4

Production of N-(p-methoxyphenyl)-2-amino-3-cyclopropylbutanoic acid

(i) (1S)-1-Methyl-2-oxo-2-tetrahydro-1-H-1-pyrrolylethyl N-(p-methoxyphenyl)-2-amino-3-cyclopropylpropanoate By the same method as Example 3, (1S)-1-methyl-2-oxo-2-tetrahydro-1-H-1-pyrrolylethyl N-(p-methoxyphenyl)-2-amino-3-cyclopropylpropanoate was obtained.

(ii) N-(p-Methoxyphenyl)-2-amino-3-cyclopropylbutanoic Acid

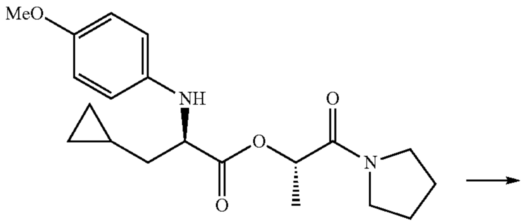

-continued

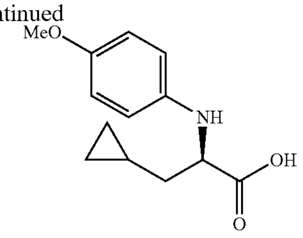

To the compound obtained in the step (i) (690 mg, 1.91 mmol), a 1N sodium hydroxide aqueous solution (8.0 mL) was added. The mixture was stirred at room temperature for 18 hours. Toluene was added to the reaction mixture, and the water layer was separated. The pH of the water layer was adjusted to 6.1 by 1N hydrochloric acid, and the mixture was stirred at room temperature for 1 hour. The precipitated white solid was separated by filtration and dried under reduced pressure to obtain the target compound (123 mg, 0.52 mmol).

Example 5

Production of methyl (2S)-α-5-(4,5,6,7-tetrahydro[3,2-c]thienopyridyl)-2-chlorophenylacetate

(i) (1R)-1-Methyl-2-oxo-2-tetrahydro-1-H-1-pyrrolylethyl (2S)-α-5-(4,5,6,7-tetrahydro[3,2-c]thienopyridyl)-2-chlorophenylacetate

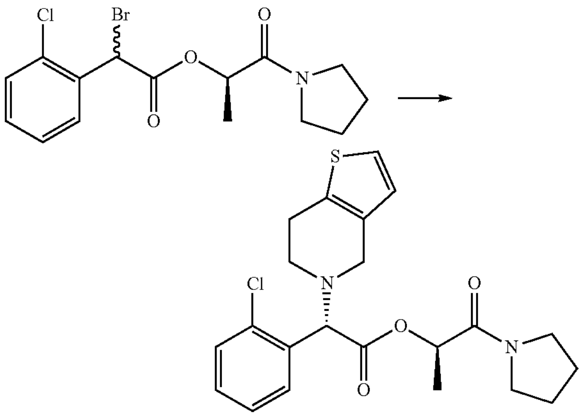

To (1R)-1-methyl-2-oxo-2-tetrahydro-1-H-1-pyrrolylethyl 2-bromo-2-(2-chlorophenyl)acetate (2.5 g, 6.5 mmol), NaI (979 mg, 6.5 mmol), triethylamine (859 mg, 8.5 mmol) and tetrahydrofuran (8 mL) were added. The mixture was cooled to 0° C. Subsequently, the tetrahydrofuran solution (8 mL) of 4,5,6,7-tetrahydrothieno[3,2-c]pyridine (1.0 g, 7.2 mmol) was added dropwise thereto over 40 minutes. After the mixture was stirred for 1 hour, a saturated sodium hydrogen sulfite aqueous solution was added thereto. The mixture was extracted with ethyl acetate. The extract was dried with anhydrous magnesium sulfate and concentrated under reduced pressure to obtain 2.7 g of the target compound (63 mmol, 96%, diastereo ratio calculated by NMR analysis=98:2).

$^1$H NMR ($CDCl_3$) δ1.41 (d, J=6.8 Hz, 3H), 1.78-2.01 (m, 4H), 2.86-3.02 (m, 4H), 3.30-3.76 (m, 6H), 5.03 (s, 1H), 5.16 (q, J=6.6 Hz, 1H), 6.67 (d, J=5.1 Hz, 1H), 7.03 (d, J=5.1 Hz, 1H), 7.21-7.31 (m, 2H), 7.39-7.41 (m, 1H), 7.71 (dd, J=7.6, 2.2 Hz, 1H)

(ii) Methyl (2S)-α-5-(4,5,6,7-tetrahydro[3,2-c]thienopyridyl)-2-chlorophenylacetate

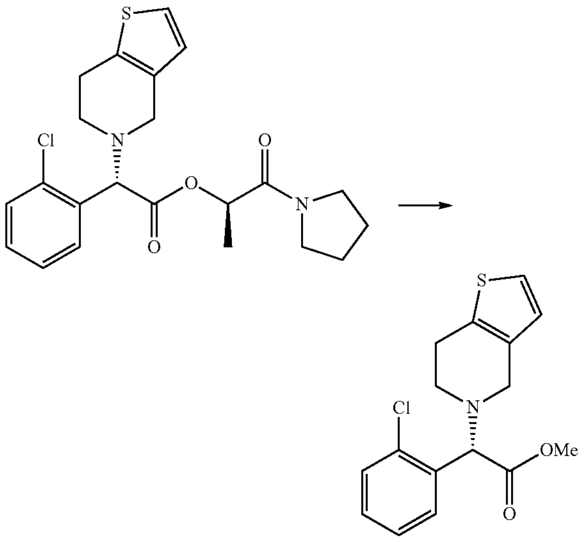

To the methanol solution (3 mL) of the compound obtained in the step (i) (1.73 g, 4.0 mmol), the methanol solution (3 mL) of aluminum chloride (1.1 g, 8.0 mmol) was added. The mixture was stirred at 60° C. for 23 hours. After the reaction solution was concentrated under reduced pressure, toluene (15 mL) and water (15 mL) were added, and the organic layer was separated. Toluene (15 mL) was further added to the water layer to obtain the organic layer. The organic layers were joined, and washed with a saturated sodium hydrogencarbonate solution. The obtained organic layer was dried with anhydrous magnesium sulfate and concentrated under reduced pressure to obtain the target compound (1.04 g, 3.2 mmol, 93% ee).

Example 6

Production of sulfuric acid salt of methyl (2S)-α-5-(4,5,6,7-tetrahydro[3,2-c]thienopyridyl)-2-chlorophenylacetate

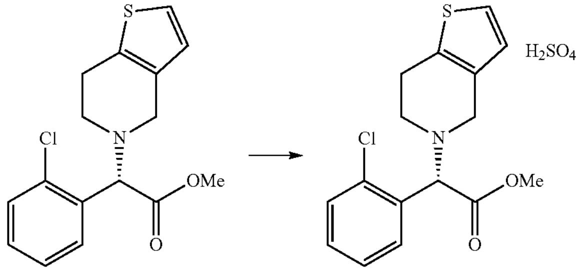

To the acetone solution (920 mL) of methyl (2S)-α-5-(4,5,6,7-tetrahydro[3,2-c]thienopyridyl)-2-chlorophenylacetate (280 g, 0.87 mol) obtained by the same method as Example 5, the acetone solution (728 mL) of concentrated sulfuric acid (12.8 g, 0.13 mol) was added. After the mixture was stirred at room temperature for 2 hours, precipitated sulfuric acid salt of α-5-(4,5,6,7-tetrahydro[3,2-c]thienopyridyl)-2-chlorophenylacetate (25 g, 0.06 mol, 36% ee) was separated by filtration. After the obtained filtrate was concentrated under reduced pressure to 1400 g, the acetone solution (728 mL) of concentrated sulfuric acid (68.3 g, 0.70 mmol) was added dropwise thereto. The mixture was stirred at room temperature for 10 hours. The precipitated solid was separated by filtration and dried under reduced pressure to obtain the target compound (287 g, 0.68 mol, 99% ee analyzed with HPLC (Column: ULTRON ES-OVM (4.6×150 mm), Wavelength: 220 nm, Flow rate: 1 mL/min, Mobile phase: PB/AN=75/25 (PB=10 mM $KH_2PO_4$ aqueous solution, AN=acetonitrile))).

Example 7

(1R)-1-Methyl-2-oxo-2-tetrahydro-1-H-1-pyrrolyl-ethyl 2-bromo-2-(2-chlorophenyl)acetate

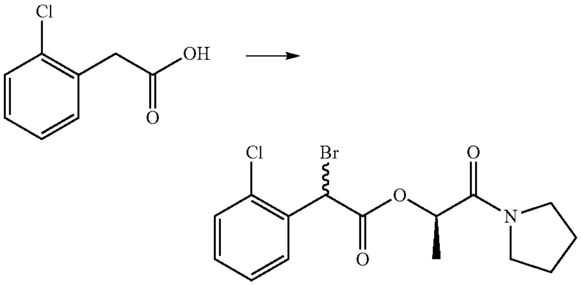

To phosphorus tribromide (28 g, 103.4 mmol), 2-chlorophenylacetic acid (44 g, 257.9 mmol) was added. The mixture was stirred at 50° C. for 1 hour. After stirring, bromine (66 g, 413.0 mmol) was added thereto at the same temperature for reaction overnight. After the reaction, toluene (200 mL) and (2R)-1-oxo-1-pyrrolidinylpropane-2-ol (40.6 g, 283.6 mmol) were added thereto at the same temperature. Subsequently, triethylamine (34 g, 336.0 mmol) was added thereto to carry out reaction for 2 hours. After the reaction, water was added thereto. After the mixture was neutralized with a 30% sodium hydroxide aqueous solution, the organic layer was separated from the water layer and the water layer was disposed of. The obtained organic layer was washed with water, and the water layer was separated and disposed of. The organic layer was concentrated under reduced pressure to obtain 83.1 g of the target compound (221.8 mmol, 86%).

$^1H$ NMR ($CDCl_3$) δ1.44 (d, J=6.8 Hz, 3H), 1.47 (d, J=6.6 Hz, 3H), 1.80-2.03 (m, 8H), 3.30-3.65 (m, 8H), 5.23-5.29 (m, 2H), 5.96 (s, 1H), 5.98 (s, 1H), 7.23-7.39 (m, 6H), 7.78-7.81 (m, 2H)

Example 8

(1R)-1-Methyl-2-oxo-2-tetrahydro-1-H-1-pyrrolyl-ethyl 2-chloro-2-(2-chlorophenyl)acetate

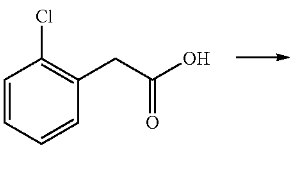

-continued

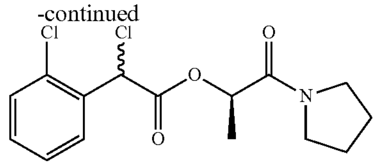

To thionyl chloride (7.7 g, 64.7 mmol), 2-chlorophenylacetic acid (10 g, 58.6 mmol) was added. The mixture was stirred at 50° C. for 3 hours. After stirring, sulfuryl chloride (12.7 g, 93.8 mmol) was added thereto at the same temperature for reaction overnight. After the reaction, toluene (45 mL) was added and (2R)-1-oxo-1-pyrrolidinylpropane-2-ol (9.2 g, 64.5 mmol) was added thereto at the same temperature. Subsequently, triethylamine (7.7 g, 93.8 mmol) was added to carry out reaction for 2 hours. After the reaction, water was added thereto and the water layer was disposed of. The obtained organic layer was washed with water, and the water layer was disposed of. The organic layer was concentrated under reduced pressure to obtain 19 g of the concentrate of the target compound.

$^1H$ NMR ($CDCl_3$) δ1.43 (d, J=6.8 Hz, 3H), 1.46 (d, J=6.6 Hz, 3H), 1.82-2.00 (m, 8H), 3.28-3.63 (m, 8H), 5.23-5.28 (m, 2H), 5.94 (s, 1H), 5.95 (s, 1H), 7.21-7.31 (m, 6H), 7.67-7.69 (m, 2H)

Example 9

(1R)-1-Methyl-2-oxo-2-tetrahydro-1-H-1-pyrrolyl-ethyl (2S)-α-5-(4,5,6,7-tetrahydro[3,2-c]thienopyridyl)-2-chlorophenylacetate To (1R)-1-methyl-2-oxo-2-tetrahydro-1-H-1-pyrrolyl-ethyl-2-bromo-2-(2-chlorophenyl)acetate (44.6 g, 119.2 mmol), NaI (1.8 g, 11.9 mmol), triethylamine (15.7 g, 155.2 mmol) and toluene (80 mL) were added. The mixture was cooled to 0° C. Subsequently, the toluene solution (24 mL) of 4,5,6,7-tetrahydrothieno[3,2-c]pyridine (18.3 g, 131.4 mmol) was added thereto dropwise over 3 hours. After the dropwise addition, the mixture was stirred for 1 hour. Next, a 20% sodium hydrogen sulfite aqueous solution was added, and the water layer was separated and disposed of. The obtained organic layer was washed with water, and the water layer was separated and disposed of. The organic layer was concentrated under reduced pressure to obtain 68 g of the concentrate of the target compound. It was confirmed with NMR analysis that the diastereo ratio of the concentrate was 97:3.

Comparative Example 1

(1S)-1-Methyl-2-oxo-2-tetrahydro-1-H-1-pyrrolyl-ethyl N-benzylhexahydro-2-pyridinecarboxylate To 1-methyl-2-oxo-2-tetrahydro-1-H-1-pyrrolylethyl 2,6-dibromohexanoate (295 mg, 0.75 mmol), NaI (225 mg, 1.5 mmol) and tetrahydrofuran (4 mL) were added. The mixture was stirred at 40° C. for 1.5 hours. Next, triethylamine (84 mg, 0.83 mmol), benzylamine (97 mg, 0.90 mmol) and tetrahydrofuran (4 mL) were added thereto. The mixture was stirred at 20° C. for 15 hours. It was confirmed with NMR analysis of the reaction solution that the conversion ration was 83% and the diastereo ratio calculated from the NMR analysis was 79:21.

Comparative Example 2

(1S)-1-Methyl-2-oxo-2-tetrahydro-1-H-1-pyrrolyl-ethyl N-allylhexahydro-2-pyridinecarboxylate TO 1-methyl-2-oxo-2-tetrahydro-1-H-1-pyrrolylethyl 2,6-dibromohexanoate (295 mg, 0.75 mmol), NaI (225 mg, 1.5 mmol), triethylamine (303 mg, 3.0 mmol) and tetrahydrofuran (4 mL) were added. Subsequently, allylamine hydrochloride (84.2 mg, 0.9 mmol) and tetrahydrofuran (4 mL) were added thereto. The mixture was stirred at 20° C. for 4 hours and then at 40° C. for 15 hours. It was confirmed with NMR analysis of the reaction solution that the conversion ratio was 100% and the diastereo ratio was 75:25.

The invention claimed is:

1. A method for producing an optically active N-protected α-amino acid ester compound, comprising the steps of a) reacting an α-haloester compound represented by the formula (1):

(1)

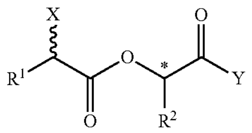

wherein, $R^1$ is an optionally substituted alkyl group having 1 to 12 carbon atoms, an optionally substituted aryl group having 6 to 14 carbon atoms, or an optionally substituted aralkyl group having 7 to 15 carbon atoms; $R^2$ is an optionally substituted alkyl group having 1 to 12 carbon atoms, an optionally substituted aryl group having 6 to 14 carbon atoms, or an optionally substituted aralkyl group having 7 to 15 carbon atoms; Y is an optionally substituted alkyloxy group having 1 to 12 carbon atoms, an optionally substituted monoalkylamino group having 1 to 12 carbon atoms, or an optionally substituted dialkylamino group having 1 to 12 carbon atoms wherein the alkyl moieties in dialkylamino group may link together to form a heterocycle; X is a halogen atom; * indicates an asymmetric carbon atom, with an amine compound represented by the formula (2):

$$HNR^3R^4 \quad (2)$$

wherein, one of $R^3$ and $R^4$ is an optionally substituted aryl group having 6-14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group; and $R^3$ may be linked with $R^4$ to form a ring, to obtain an optically active N-protected α-amino acid ester compound represented by the formula (3):

(3)

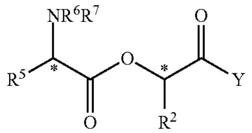

wherein, $R^5$ is an optionally substituted alkyl group having 1 to 12 carbon atoms, an optionally substituted aryl group having 6 to 14 carbon atoms, or an optionally substituted aralkyl group having 7 to 15 carbon atoms or may be linked with $R^6$ to form a ring; one of $R^6$ and $R^7$ is an optionally substituted aryl group having 6 to 14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group or $R^6$ may be linked with $R^5$ to form a ring; $R^7$ may be linked with $R^6$ to form a ring; $R^2$ and Y are the same as the above; * indicates an asymmetric carbon;

b) conducting ester exchange of the above N-protected α-amino acid ester compound represented by the formula (3) with an alcohol represented by the formula (4):

$$R^8OH \quad (4)$$

wherein, $R^8$ is an optionally substituted alkyl group having 1 to 12 carbon atoms, an optionally substituted aryl group having 6 to 14 carbon atoms, or an optionally substituted aralkyl group having 7 to 15 carbon atoms;

wherein the optically active N-protected α-amino acid ester compound is represented by the formula (5):

(5)

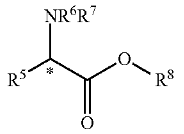

wherein, $R^5$, $R^6$, $R^7$, $R^8$ and * are the same as the above.

2. The production method according to claim 1, wherein $R^2$ is a methyl group.

3. The production method according to claim 1, wherein Y is a pyrrolidinyl group.

4. The production method according to claim 1, wherein the reaction of the step a) is carried out in the presence of an iodine ion.

5. The production method according to claim 1, wherein the ester exchange reaction is carried out using an acid.

6. The production method according to claim 5, wherein the ester exchange reaction is carried out using a Lewis acid.

7. The production method according to claim 6, wherein the ester exchange reaction is carried out using at least one of an aluminium salt and a titanium salt.

8. The production method according to claim 1, wherein $R^1$ and $R^5$ are 2-chloro phenyl groups.

9. The production method according to claim 1, wherein the amine represented by the formula (2) is 4,5,6,7-tetrahydrothieno[3,2-c]pyridine.

10. The production method according to claim 1, wherein the alcohol represented by the formula (4) is methanol.

11. The production method according to claim 1, comprising the steps of:

reacting a carboxylic acid represented by the formula (6):

(6)

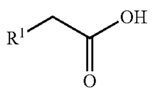

wherein, $R^1$ is the same as defined in claim 1, with phosphorus tribromide and bromine, to obtain a compound represented by the formula (7):

(7)

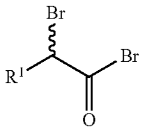

wherein, $R^1$ is the same as the above, and reacting the compound represented by the formula (7) with an alcohol represented by the formula (8):

(8)

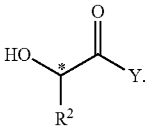

wherein, $R^2$ and Y are the same as defined in claim 1; * indicates an asymmetric carbon, to obtain the α-haloester compound represented by the formula (1).

12. An α-haloester compound represented by the formula (9):

(9)

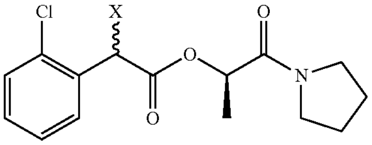

wherein, X is a halogen atom.

13. An optically active N-protected α-amino acid ester compound represented by the formula (10):

(10)

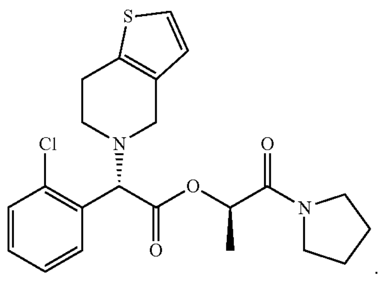

14. A method for producing an optically active α-amino acid compound, comprising the steps of a) reacting an α-haloester compound represented by the formula (1):

(1)

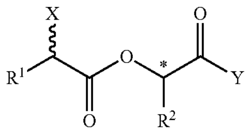

wherein, $R^1$ is an optionally substituted alkyl group having 1 to 12 carbon atoms, an optionally substituted aryl group having 6 to 14 carbon atoms, or an optionally substituted aralkyl group having 7 to 15 carbon atoms; $R^2$ is an optionally substituted alkyl group having 1 to 12 carbon atoms, an optionally substituted aryl group having 6 to 14 carbon atoms, or an optionally substituted aralkyl group having 7 to 15 carbon atoms; Y is an optionally substituted alkyloxy group having 1 to 12 carbon atoms, an optionally substituted monoalkylamino group having 1 to 12 carbon atoms, or an optionally substituted dialkylamino group having 1 to 12 carbon atoms wherein the alkyl moieties in dialkylamino group may link together to form a heterocycle; X is a halogen atom; * indicates an asymmetric carbon atom, with an amine compound represented by the formula (2):

$HNR^3R^4$ (2)

wherein, one of $R^3$ and $R^4$ is an optionally substituted aryl group having 6 to 14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group; and $R^3$ may be linked with $R^4$ to form a ring, to obtain an optically active N-protected α-amino acid ester compound represented by the formula (3):

(3)

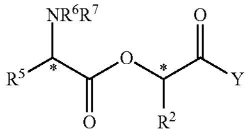

wherein, $R^5$ is an optionally substituted alkyl group having 1 to 12 carbon atoms, an optionally substituted aryl group having 6 to 14 carbon atoms, or an optionally substituted aralkyl group having 7 to 15 carbon atoms or may be linked with $R^6$ to form a ring; one of $R^6$ and $R^7$ is an optionally substituted aryl group having 6 to 14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group or $R^6$ may be linked with $R^5$ to form a ring; $R^7$ may be linked with $R^6$ to form a ring; $R^2$ and Y are the same as the above; * indicates an asymmetric carbon;

c) cleaving the substituent group on the N atom of the N-protected α-amino acid ester compound represented by the formula (3), to obtain an α-amino acid ester compound represented by the formula (11):

(11)

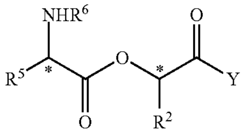

wherein, $R^2$, $R^5$, $R^6$, Y and * are the same as the above;

d) hydrolyzing the α-amino acid ester compound represented by the formula (11);

wherein the optically active α-amino acid compound is represented by the formula (12):

(12)

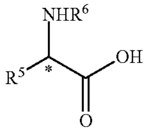

wherein, $R^5$, $R^6$ and * are the same as the above.

15. The production method according to claim 14, wherein $R^2$ is a methyl group.

16. The production method according to claim 14, wherein Y is a pyrrolidinyl group.

17. The production method according to claim 14, wherein the reaction of the step a) is carried out in the presence of an iodine ion.

18. The production method according to claim 14, wherein at least one of $R^3$ and $R^4$ is an aryl group.

19. The production method according to claim 18, wherein at least one of $R^3$ and $R^4$ is a p-methoxyphenyl group or an o-methoxyphenyl group.

20. The production method according to claim 14, wherein $R^1$ is an alkyl group.

21. The production method according to claim 19, wherein at least one of bromine, trichloroisocyanuric acid, N-bromosuccinimide, N-chlorosuccinimide and $H_5IO_6$ is used for cleaving the substituent group on the N atom for deprotection.

22. A method for producing an optically active N-protected α-amino acid compound, comprising the steps of a) reacting an α-haloester compound represented by the formula (1):

(1)

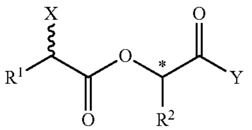

wherein, $R^1$ is an optionally substituted alkyl group having 1 to 12 carbon atoms, an optionally substituted aryl group having 6 to 14 carbon atoms, or an optionally substituted aralkyl group having 7 to 15 carbon atoms; $R^2$ is an optionally substituted alkyl group having 1 to 12 carbon atoms, an optionally substituted aryl group having 6 to 14 carbon atoms, or an optionally substituted aralkyl group having 7 to 15 carbon atoms; Y is an optionally substituted alkyloxy group having 1 to 12 carbon atoms, an optionally substituted monoalkylamino group having 1 to 12 carbon atoms, or an optionally substituted dialkylamino group having 1 to 12 carbon atoms wherein the alkyl moieties in dialkylamino group may link together to form a heterocycle; X is a halogen atom; * indicates an asymmetric carbon atom, with an amine compound represented by the formula (2):

$$HNR^3R^4 \quad (2)$$

wherein, one of $R^3$ and $R^4$ is an optionally substituted aryl group having 6 to 14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group; and $R^3$ may be linked with $R^4$ to form a ring, to obtain an optically active N-protected α-amino acid ester compound represented by the formula (3):

(3)

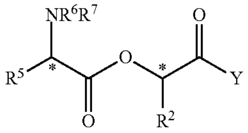

wherein, $R^5$ is an optionally substituted alkyl group having 1 to 12 carbon atoms, an optionally substituted aryl group having 6 to 14 carbon atoms, or an optionally substituted aralkyl group having 7 to 15 carbon atoms or may be linked with $R^6$ to form a ring; one of $R^6$ and $R^7$ is an optionally substituted aryl group having 6 to 14 carbon atoms, and the other is a hydrogen atom, an optionally substituted alkyl group having 1 to 12 carbon atoms, an optionally substituted aryl group having 6 to 14 carbon atoms, an optionally substituted aralkyl group having 7 to 15 carbon atoms, a sulfonyl group or a carbonyl group or $R^6$ may be linked with $R^5$ to form a ring; $R^7$ may be linked with $R^6$ to form a ring; $R^2$ and Y are the same as the above; * indicates an asymmetric carbon;

e) hydrolyzing the N-protected α-amino acid ester compound represented by the formula (3);

wherein the optically active N-protected α-amino acid compound is represented by the formula (13):

(13)

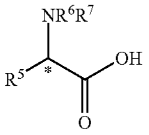

wherein, $R^5$, $R^6$, $R^7$ and * are the same as the above.

23. The production method according to claim 22, wherein $R^2$ is a methyl group.

24. The production method according to claim 22, wherein Y is a pyrrolidinyl group.

25. The production method according to claim 22, wherein at least one of $R^3$ and $R^4$ is an aryl group.

26. The production method according to claim 22, wherein $R^1$ is an alkyl group.

27. The production method according to claim 22, wherein the reaction of the step a) is carried out in the presence of an iodine ion.

* * * * *